(12) United States Patent
Schultz

(10) Patent No.: US 6,256,522 B1
(45) Date of Patent: *Jul. 3, 2001

(54) SENSORS FOR CONTINUOUS MONITORING OF BIOCHEMICALS AND RELATED METHOD

(75) Inventor: Jerome S. Schultz, Pittsburgh, PA (US)

(73) Assignee: University of Pittsburgh of the Commonwealth System of Higher Education, Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/516,257

(22) Filed: Aug. 17, 1995

Related U.S. Application Data

(62) Division of application No. 07/980,027, filed on Nov. 23, 1992, now abandoned.

(51) Int. Cl.[7] .................................................. A61B 5/00
(52) U.S. Cl. ........................ 600/317; 600/342; 600/310; 600/322
(58) Field of Search ........................... 728/633, 4, 664–6; 250/364, 365; 482/55; 356/39, 418, 415; 600/310, 317, 342

(56) References Cited

U.S. PATENT DOCUMENTS

| 3,123,866 | 3/1964 | Stewart | 19/97 |
|---|---|---|---|
| 3,461,856 | 8/1969 | Polanyi | 128/2 |
| 3,638,639 | 2/1972 | Merrill et al. | 128/2 F |
| 3,785,772 | 1/1974 | Coggeshall | 23/253 R |
| 3,787,119 | 1/1974 | Rybak | 356/73 |

(List continued on next page.)

OTHER PUBLICATIONS

Wolfbeis, Fibre–Optic Sensors in Biomedical Sciences, Pure & Appl. Chemistry, vol. 59, No. 5, pp. 663–672 (1987).

Fischer et al., Assessment of Subcutaneous Glucose Concentration: Validation of the Wick Technique as a Reference for Implanted Electrochemical Sensors in Normal and Diabetic Dogs, Diabetologia, 30: 940–945 (1987).

Van Der Putten et al., A Modelling Approach to the Detection of Subcutaneous Tumors by Haematoporphyrin–Derivative Fluorescence, Phys. Med. Biol., vol. 28, No. 6, pp. 639–645 (1983).

Meadows et al., Fiber–Optic Biosensors Based on Fluorescence Energy Transfer, Talanta, vol. 35, No. 2, pp. 149–150 (1988).

*Primary Examiner*—Robert L. Nasser
(74) *Attorney, Agent, or Firm*—Arnold B. Silverman; Eckert Seamans Cherin & Mellott, LLC

(57) ABSTRACT

Apparatus and method for measuring properties of certain analytes are provided. The apparatus includes a sensor capsule having a processing chamber defined by a wall which in one embodiment has a semi-permeable membrane permeable to the analyte as at least a portion thereof. Receptor material is disposed within the chamber and is capable of chemically interacting with the analyte. In one embodiment, at least a portion of the sensor is translucent. A light source, which may be an optical fiber, causes light to impinge on a translucent portion of the capsule and pass therethrough. Responsive fluorescent light is generated and emitted. This light may be received by detector means and processed in a conventional manner to determine concentration of the analyte. A dye-labelled analog-analyte may be provided within the chamber. Both the receptor material and analog-analyte are of such size that they will not pass through the semi-permeable membrane although the analyte can. The invention is particularly suited to use of the capsule as an implantable element which is physically separated from the light source and detector and can be placed underneath the skin. In another embodiment, a receptor reagent and a receptor are covalently bonded to a stable polymer structure and a semi-permeable membrane is not required.

4 Claims, 2 Drawing Sheets

U.S. PATENT DOCUMENTS

| | | | |
|---|---|---|---|
| 3,939,350 | 2/1976 | Kronick et al. | 250/365 |
| 4,344,438 | 8/1982 | Schultz | 128/634 |
| 4,558,014 | 12/1985 | Hirschfeld et al. | 436/527 |
| 4,572,106 | 2/1986 | Mills | 119/14.47 |
| 4,577,109 | 3/1986 | Hirschfeld | 250/461.1 |
| 4,755,667 | 7/1988 | Marsoner et al. | 250/227 |
| 4,815,843 | 3/1989 | Tiefenthaler et al. | 356/128 |
| 4,849,172 | 7/1989 | Yafuso et al. | 422/55 |
| 4,857,273 | 8/1989 | Stewart | 422/68 |
| 4,861,727 | 8/1989 | Hauenstein et al. | 436/136 |
| 4,877,747 | 10/1989 | Stewart | 436/525 |
| 4,892,383 | 1/1990 | Klainer et al. | 350/96.29 |
| 4,892,640 | 1/1990 | Wolfbeis et al. | 204/418 |
| 4,954,318 | 9/1990 | Yafuso et al. | 422/59 |
| 4,999,306 | 3/1991 | Yafuso et al. | 436/68 |
| 5,143,066 | 9/1992 | Komives et al. | 128/634 |
| 5,342,785 | 8/1994 | Chick et al. | 128/633 |

SENSORS FOR CONTINUOUS MONITORING OF BIOCHEMICALS AND RELATED METHOD

This is a division of application Ser. No. 07/980,027 filed Nov. 23, 1992 now abandoned.

BACKGROUND OF THE INVENTION

1. Field of the Invention

This invention relates to devices for measuring the concentration of certain biochemical constituents in a patient. More particularly, the invention also relates to sensor units which may be placed under a patient's skin and which are used in conjunction with remote detection means to sense properties of a sample analyte.

2. Description of the Prior Art

It has become increasingly important in analytical and clinical chemistry to have the capability of remote sensing of chemical and physical parameters. Some methods of performing this type of sensing have been known, such as potentiometry, amperometry, piezoelectric mass determination, conductivity and measurement of reaction enthalpy.

In addition to these methods, optical fibers can be used for remote sensing of analytes and other substances. Optical sensors have certain advantages over electrochemical sensors. For example, optical sensors are immune to electromagnetic interferences. Further, the use of optical fibers can be advantageous when the samples are relatively inaccessible, for instance, in case of in vivo tests. Optical fiber wave guides allow the transportation of an optical signal over large distances from the sample to an associated meter, for example. Optical fibers can be exposed to varying environments without suffering substantial destruction or deterioration as a result. For a general discussion of sensors and of optical fiber sensors in particular see Wolfbeis, Fibre-optic Sensors in Biomedical Sciences, *Pure and Appl. Chemistry*, Vol. 59, No. 5 pp. 663–672 (1987). See also U.S. Pat. Nos. 4,954,318 and 4,999,306.

It has been known to provide optical fiber sensors of various types. The disclosure of U.S. Pat. No. 4,334,438, is hereby incorporated herein by reference. This patent relates to a fiber optic sensor having a chamber containing a dialysis membrane which allows selected plasma constituents to pass therethrough and enter the chamber. The chamber contains specific receptor sites in the form of binding agents each of which reversibly binds with one of the plasma constituents. The chamber also contains competing ligands which are dye-labeled. They compete with the plasma constituents for the specific receptor sites on the binding agents. The competing ligands are chosen for their particular optical properties and molecular size so that they do not escape back out of the sensor into the bloodstream. The intensity of light emitted from or absorbed by the receptor-site/competing ligand complexes or the free competing ligand alone can be measured by a fluorimeter. This measurement gives a quantitative indication of the concentration of plasma constituents in the blood.

One limitation of the system of U.S. Pat. No. 4,334,438 is that the response time is on the order of minutes due to the time it takes for diffusion of the molecules being studied across the membrane and along the chamber. Further, as the fluorescently labeled compound is bound to the wall, the optical fiber must be inserted exactly straight inside the hollow fiber so that the amount of baseline fluorescence due to the dye-labeled competing ligand bound to the wall is minimized. Further, the skin of the membrane must remain immersed in a buffer solution during storage of the sensor. Otherwise, if it is exposed to air, the membrane begins to dry and subsequent diffusion of the analyte into the sensor is dramatically affected. Because of this, the assembly must be glued together while it is submerged in the buffer. The glue seams must form a tight seal because with any leak, the chemical constituents of the sensor can escape. The optical fiber within the hollow fiber configuration can also exhibit lack of stability such that any relative movement between the two fibers while in use affects the signal response. In addition, during assembly the proteins which are immobilized are pumped through the fiber under the influence of pressure. This flow method results in variations in the amount of immobilized material along the inside wall, due to variations in the spongy surface causing a variability in the calibration curves between sensors during manufacture. There remains a need, therefore, for a sensor which overcomes these disadvantages.

Systems such as the one described hereinabove also present another problem. If the device is to be used on a patient, a chronic invasive connection through the skin must be maintained. This can result in a host of problems and annoyances when taking measurements. There remains a need, therefore, for a device that may be used in vivo without the need for chronic connections through the skin.

It has also been known to provide other types of fiber optic sensors. For example, U.S. Pat. No. 4,892,383 discloses a fiber optic sensor which includes a modular reservoir cell body and a semi-permeable membrane, however, the sensor requires use of a reagent which precludes reversibility. See also U.S. Pat. No. 4,892,640 which discloses a sensor for determining electrolytic concentrations using an ion selective membrane.

U.S. Pat. No. 4,849,172 discloses an optical sensor having a gas permeable silicone matrix that contains a high concentration of an optical indicator consisting essentially of a mixture of derivatives of a polynuclear aromatic compound. U.S. Pat. No. 4,857,273 discloses another type of sensor involving enhancement of a light signal response by incorporating a partially reflecting, partially transmitting medium between a coupling structure and an optically dense body.

Optical sensors based on generating a resonance signal in a metallic medium have also been known. See U.S. Pat. No. 4,877,747. Other sensors based on detection of refractive index charges in gaseous liquids, solids or porous samples have been known. See U.S. Pat. No. 4,815,843 and U.S. Pat. No. 4,755,667. Sensors for measuring salt concentrations have also been known. U.S. Pat. No. 4,572,106.

U.S. Pat. No. 4,577,106 discloses a remote multi-position information gathering system for obtaining thermometric information from remote locations using fiber optics.

U.S. Pat. No. 4,861,727 discloses a luminescent oxygen sensor using a lanthanide complex. U.S. Pat. No. 4,558,014 discloses assay apparatus employing fluorescence.

Other methods of measuring concentrations of biochemicals in blood include withdrawing blood from the patient for analysis. For example, U.S. Pat. No. 3,785,772 discloses a device having a pair of syringes to withdraw blood from a patient, and a dialysis membrane to separate a particular blood constituent from the blood, a reactant which reacts with the chosen blood constituent to form a reactant-blood constituent complex the concentration of which is proportional to the concentration of the blood constituent. This system requires replacement of the reactant after each measurement because the reactant and the blood constituent form an irreversible complex. In addition, the system cannot measure an instantaneous change in the concentration of the blood constituent because of the time taken to remove the blood from the body and obtain a reaction with the reactant.

U.S. Pat. No. 3,638,639 also discloses measurement of blood constituents outside the body. In this system, a catheter is inserted into the blood and lipids are passed through a membrane in the catheter and are dissolved in a solvent which is removed from the body to be analyzed.

U.S. Pat. No. 3,939,350 shows a system for carrying out immunoassays using fluorescence to indicate the presence of a ligand to be detected. An analog liquid is bound to a transparent sheet and contacted with an aqueous assay solution containing the ligand to be detected associated with fluorescent molecules. The ligands become bonded to the sheet and light is passed therethrough to cause fluorescence.

U.S. Pat. Nos. 3,123,866, 3,461,856 and 3,787,119, all disclose means to measure properties of the blood in vivo. These systems comprise optical catheters inserted into the blood for measuring the intensity of light reflected from the blood thereby indicating the blood's oxygen content. None of the aforementioned patents, however, are specifically designed for measuring the concentration of plasma constituents, such as glucose, in a continuous, reversible manner.

It has also been known to employ oximeters, which are photoelectric photometers, to noninvasively estimate the extent of blood oxygenation. These systems are noninvasive and employ no reagents.

U.S. Pat. No. 5,143,066 owned by the assignee of the present invention is expressly incorporated by reference herein. It discloses a system for measuring properties of certain substances designated as analytes. A probe housing has an optical fiber associated therewith and has a membrane which is permeable to the analyte being studied. The housing has a reflective surface member disposed between the optical fiber and membrane to define a dark chamber which does not allow light from the optical fiber to enter or exit the chamber. A dye-labelled analog-analyte can pass through the reflective member to permit it to enter an adjacent light chamber where measurements related to the concentration of the analyte may be made. Excitation light from an optical fiber is received within the light chamber. Immobilized receptors are provided within the housing preferably in the dark chamber. The dye-labelled analog-analyte and analyte compete to bind with the immobilized receptors. The dye-containing analog-analyte molecules which do not bind to immobilized receptors pass through the reflective surface member to the light chamber. A light source acting through the optical fiber creates responsive fluorescent light to be emitted by the dye-containing analog-analyte with such responsive light being carried to the detector means. The detector means employ this fluorescent light to determine concentration of the analyte in the sample. In one embodiment, an in vivo sensor which may be placed under the skin is employed. This system, however, employs two chambers alone with fiber optic means and a reflective divider between the two chambers.

Despite these prior art methods and devices, there remains a need for a sensor which has increased sensitivity and a shorter response time. Further, there remains a need for a device where the active element is of shorter length and a sensor which is easier to assemble than conventional designs. There remains a further need for a device and method which may be used to measure either free dye-containing molecules or bound dye-containing molecules and which has the capability of providing continuous monitoring of the concentration of an analyte.

There is also a need for a sensor device used for the continuous monitoring of biochemicals which may be used in vivo without the need for chronic connections through the patient's skin. Therefore, there remains a need for a less-invasive device for in vivo sensing of analyte properties which does not require the use of chronic connections through the skin.

SUMMARY OF THE INVENTION

These and other needs are satisfied by the device and method of the present invention.

The sensor is placed in contact with the substance to be analyzed, referred to herein as the analyte. The analyte may be any soluble molecule which is mobile and can pass through a dialysis membrane. It may be a water soluble molecule. The analyte is brought in contact with receptors which may be immobilized receptors. There, the analyte competes with a dye-labeled substance which is similar in chemical properties to the analyte. This dye-labeled substance, or substance employing another marker, will be referred to herein as the "analog-analyte". In lieu of dye-labelling, another marker that can be determined remotely such as a radioactive isotope or paramagnetic material could be employed. The analyte and the analog-analyte compete to bind with the receptors. In the dye-labelled embodiment, a light source illuminates the sensor interior. Upon excitation, the fluorescent dye causes light to be emitted from the dye-containing analog-analyte molecules, and this light signal is then transmitted to detection means. The magnitude of the signal is different for bound and free analog-analyte molecules. The measurements are then used to determine the concentration of the particular analyte contained in the sample.

To eliminate chronic connections through the skin, several embodiments of the present invention are disclosed in which the probe housing is a sensor unit physically separate from any optical fiber, light source, or detection means. In one embodiment of the present invention, a probe housing contains a permeable membrane and has a light reflective surface. It may be a separate sensor unit. This sensor unit may be placed under a patient's skin. The light source and detection means used with this embodiment need not utilize optical fibers, although the use of optical fibers is preferred.

In another embodiment of the present invention in which the probe housing is an independent sensor unit to be placed under the skin, a reflective surface member is absent from within the sensor unit and is disposed adjacent to and underneath the sensor unit. The light source and detection means used with this embodiment need not utilize optical fibers, although the use of optical fibers is preferred.

In another embodiment of the present invention, an independent sensor unit to be placed under the skin which does not utilize a reflective surface member at all is provided. This embodiment may measure optical properties of the system or the receptor material. The receptor material and analog-analyte may be selected so that other properties of the system may also be measured by detection means.

In another embodiment, a receptor and a reporter reagent are covalently bonded to the exterior of a polymer structure and the analyte may be a macromolecule.

It is an object of the invention to provide a sensor with effective sensitivity to dye-containing analog-analytes, and which may be utilized for studying either bound or free dye-containing substances, in a continuous, reversible manner.

It is another object of the invention to provide a sensor which is smaller but still provides desired sensitivity.

It is another object of the invention to provide a sensor which uses a membrane that eliminates or minimizes the need for hollow fiber membranes as well as reducing the number of glue seals required.

It is another object of the invention to provide a sensor which is easy to manufacture and easy to use and handle by inexperienced personnel.

It is another object of the invention to provide a sensor which provides durability.

It is a further object of the invention to provide a sensor unit which may be placed under the skin and allow for remote sensing of analytes.

It is another object of the present invention to provide such a system which does not require chronic connections through the patient's skin.

It is a further object of the invention to provide a device which has a stable response for long periods of time.

It is yet a further object of the invention to provide a method of analyzing and measuring chemical substances which is reliable and easy to employ in a variety of settings.

These and other objects of the invention will be fully understood from the following description of the invention with reference to the drawings appended to this Application.

DESCRIPTION OF THE PREFERRED EMBODIMENTS

As used herein, "patient" means any animal, including humans.

Figure 1:
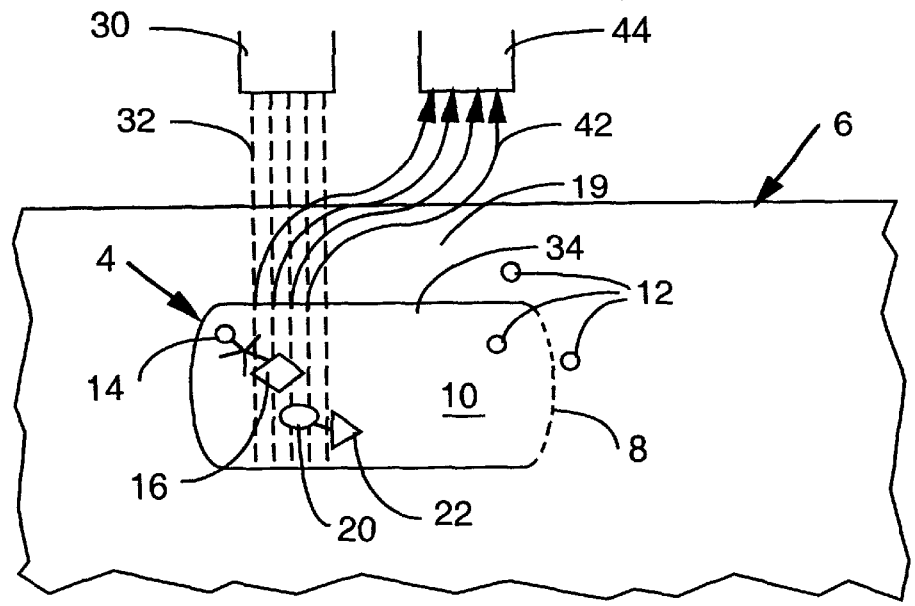
FIG. 1 is a schematic cross-sectional illustration of an embodiment of the present invention which is placed under the skin.

In one embodiment as shown in FIG. 1 of the present invention the probe housing is a separate unit which need not employ an optical fiber or a reflective surface member. In this embodiment the sensor unit 4 is transparent or translucent. This sensor unit 4 has a capsule with a single zone. The sensor unit 4 comprises a capsule defining a chamber preferably about 1 to 2 mm in diameter and having a height of about 1 to 10 mm. The capsule wall thickness is preferably about 0.025 to 0.2 mm. At least a portion of the capsule 4 is a semi-permeable membrane. The semi-permeable membrane can be made of, for example, cellulose or polysulfone. This semi-permeable membrane allows the passage of the analytes of interest into the capsule interior, while retaining materials that cause a response. The remainder of the capsule can be made of, for example, polymers, metals, or ceramics. Examples of such polymers include nylon or polymethacrylate. In general, it is preferred to select a membrane pore size such that the pore size is the smallest size that will permit analyte passage while resisting entry of undesired extraneous materials into the capsule 4.

The receptor material of this embodiment may be fully mobile within the chamber. If the receptor material is fully mobile, diffusion of the receptor material out of the chamber is resisted by the semi-permeable membrane. Alternatively, the receptor material may be immobilized to a gel within the chamber or be bound to an inner wall of the semi-permeable membrane or anywhere else within the chamber. When immobilized to a gel, molecules of the receptor material are covalently bonded to strands of polymers which are cross-linked to each other to form a gel. Examples of gel forming polymers include polyacrylamide, cellulose, polyethylene glycol, and gelatin. In this embodiment, the sensor unit may also be labeled with a dye.

The probe housing also contains an "analoganalyte". As used hereinafter, the term "analog-analyte" includes a competing substance which has properties similar to the analyte. The analyte may be any mobile molecule including any water-soluble biochemical. The analog-analyte competes with the analyte for the opportunity to bind with a receptor. As it has properties similar to the analyte used in the particular application, it is called an "analog-analyte." The analog-analyte is chosen for its particular optical properties and molecular size, so that it will adequately compete with analyte for receptor sites. If an analog-analyte for a particular analyte does not exist, one can be created by binding (a) a large protein, such as bovine serum albumin or a polymer, such as a starch or polyethylene glycol with (b) the analyte in a manner which would be understood by those skilled in the art.

The solution within the capsule will preferably be the equivalent of plasma. As a result of the semi-permeable membrane, there will be free exchange of salts and metabolites with the exterior of the capsule. Proteins will not, however, be free to enter the capsule.

The reaction which takes place within the capsule can be summarized by the following equations:

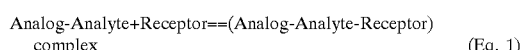

Analog-Analyte+Receptor==(Analog-Analyte-Receptor) complex  (Eq. 1)

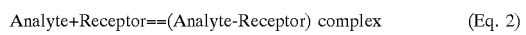

Analyte+Receptor==(Analyte-Receptor) complex  (Eq. 2)

In accordance with Equation 1, the analog-analyte binds with a receptor to form an analog-analyte-receptor complex. When the analyte molecules are introduced into the system by diffusion through the membrane, they may then bind with that receptor to form an analyte-receptor complex as stated in Equation 2. This frees the previously bound analog-analyte. The analog-analyte molecules fluoresce in response to excitation energy sent into the sensor. For a general discussion of bioreceptors as used within sensors, see Schultz, "Sensitivity and Dynamics of Bioreceptor based Biosensors", *Annals of the New York Academy of Sciences*, Vol. 506 (1987).

In order to cause fluorescence, and thereby allow detection, the analog-analyte should be fluorescently labeled by covalent coupling with an appropriate dye as is known to those skilled in the art. A suitable dye-containing analog-analyte is Fluorescein Isothiocyanate-dextran known as FITC-dextran. Other dye containing analog-analytes are FITC anti-rabbit IgG as disclosed by Tromberg et al., *Anal. Chem.*, Vol. 59 pp. 1226–1230 (1987); and phycobiliprotein disclosed by Oi et. al, *J. Cell Biol.*, Vol. 93, p. 981 (1982).

Although specific examples have been cited, the principle of the present invention applies equally to any analyte-receptor system whose equilibrium binding constant permits free exchange with the analog-analyte.

The capsule may be sealed mechanically by screwed joints plus O-rings, but is preferably sealed by adhesion or heat sealing. A preferred embodiment involves the use of preformed hollow fibers suitably loaded with the sensor reagents as by a hypodermic needle with the ends subsequently sealed. The hollow fibers may be hollow dialysis fibers of the type currently employed in artificial kidneys, cut to the desired length. After introduction of the sensor reagents, they may be sealed by suitable adhesive such as an epoxy, for example, or by solvent or thermally induced self-bonding. An alternate approach would be to provide a small generally cylindrical hollow member having one integral end. The other end could be closed by a suitable membrane held in place by a retainer ring.

Referring to FIG. 1, the sensor unit is preferably placed about 1 mm under the skin. As the skin is capable of being penetrated by light, a light source 30 would be used to shine excitation light 32 onto the area 19 of the skin 6 above sensor unit 4 and detector 44 could then be used to measure the emission signal. The degree of interaction of the analyte with the materials within the capsule is monitored remotely by detector 44 which measures some property of the system, such as, for example: (a) absorption of light (ultraviolet, visible, or infrared), (b) changes in spectrum of one of the materials (ultraviolet, visible, or infrared), or (c) fluorescence of the materials. If desired, a reflective surface may be employed and be positioned within a lower wall of the sensor or positioned thereunder. The reflective surface member increases the sensitivity of the sensor by reflecting light emitted from the sensor towards the detector means 44.

The sensor unit 4 may be placed under the skin 6 of a patient by making an incision and inserting the sensor unit 4 manually or by using a needle device preferably about 1 mm under the skin surface. A number of such devices are known to those skilled in the art for the placement of drug release formulations. The reflective surface member may be placed adjacent to and underneath the sensor unit 4 by similar means. The reflective surface member increases the sensitivity of the sensor by reflecting light 42 emitted from the sensor unit 4 up through the skin 6 towards the detection means.

The sensor unit 4 is illuminated remotely by a light source 30 above the skin. The light source can be, for example, a tungsten lamp, laser, or halogen lamp and is preferably a Light emitting diode at the most sensitive wavelength. There is enough transparency at a depth of about 1 mm under the skin 6 to measure the desired optical properties. While not the preferred embodiment, the light source 30 and the detection means 44 can illuminate and measure optical properties from the capsule 4 without the use of optical fibers. Optical fibers are, however, preferably utilized. The optical fibers may be a single optical fiber or a bundle thereof with our without an opaque outer coating.

The chamber 10 defined within sensor unit or capsule 4 may contain a receptor material and a dye-labeled analog-analyte as disclosed in previous embodiments hereinbefore. Alternatively, the desired materials may be limited to a receptor material. This latter approach can be used when some property of the analyte or the receptor material undergoes a measurable change when the analyte and the receptor material bind. For example, blood oxygenation may be measured by sensing the change in the spectrum of hemoglobin (the receptor material) from blue to red when the hemoglobin binds to oxygen (the analyte). Depending on the property being measured, the receptor material may be dye-labeled.

In another embodiment of the present invention in which the probe housing is a unit separate from the detection means, the reflective surface may be eliminated entirely. Again, this sensor unit chamber does not possess two zones, one illuminated and one dark, but is a single zone. As in the previous embodiment, the sensor unit 4 is a capsule defining a generally cylindrical chamber preferably about 1 to 2 mm in diameter and about 1 to 10 mm in height. At least a portion of the capsule is a semi-permeable membrane. The semi-permeable membrane can be made of, for example, cellulose or polysulfone. This semi-permeable membrane allows the passage of the analytes of interest, while retaining the materials that cause a response. The remainder of the capsule can be made of, for example, polymers, metals, or ceramics. Examples of suitable polymers include nylon or polymethacrylate.

The chamber may again contain a receptor material and a dye-labeled analog-analyte or simply a receptor material. In either case, the receptor material may be dye-labeled.

The receptor material of the present embodiment may also be fully mobile within the chamber. If the receptor material is fully mobile, diffusion of the receptor material out of the chamber is resisted by the semi-permeable membrane. Alternatively, the receptor material may be immobilized to a gel within the chamber or bound to an inner wall of the semi-permeable membrane or anywhere else within the chamber. When immobilized to a gel, molecules of the receptor material are covalently bonded to strands of polymers which are cross-linked to each other to form a gel. Examples of gel forming polymers include polyacrylamide, cellulose, polyethylene glycol, and gelatin. Once the chamber is loaded with the desired materials, the capsule is sealed.

The degree of interaction of the analyte with the materials within the capsule is monitored remotely by detection means 44 which measure some property of the system, such as, for example: (a) absorption of light (ultraviolet, visible, or infrared), (b) changes in spectrum of one of the materials (ultraviolet, visible, or infrared), (c) fluorescence of the materials, (d) electrical conductivity, (e) electrical capacity, (f) electrical frequency, (g) magnetism, (h) effect of the system on polarized light, or (i) production of detectable compounds by enzymes.

The detection means 44 may be any means suitable to convert the light emerging from sensor 4 into concentration information. A suitable approach is the fluorimeter system disclosed in U.S. Pat. No. 5,143,066 in which the present inventor is a co-inventor.

The information can be analyzed by a microcomputer such as an IBM-PC which is programmed in a suitable manner as will be readily understood by those skilled in the art. The analysis involves measuring a signal corresponding to the amount of free fluorescent analog-analyte 14 which diffuses into illuminated region (FIG. 1). When this free analog-analyte 14 fluoresces the light signal 42 is emitted. The amount of free analog-analyte 14 is proportional to the concentration of analyte 12 in the sample. In this way the concentration of analyte 12 present can be accurately determined.

If an optical property of the system is being measured, the sensor unit 4 is illuminated remotely by a light source 30 above the skin as discussed hereinafter. Also, at least a portion of the capsule 4 is transparent or translucent and faces the patient's skin 6 when the sensor unit 4 is placed under the skin. The semi-permeable membrane may be the transparent or translucent portion of the capsule 4. It is preferable that the entire capsule be transparent so that orientation with respect to skin 6 is not critical. There is enough transparency at a depth of about 1 mm under the skin to measure optical properties. The capsule is preferably sufficiently rigid to maintain the desired shape.

Referring to FIG. 1 there is shown a sensor 4 which is positioned in vivo about 1 to 2 millimeters under the skin 6 in region 19. In this embodiment, fluorescent light 42 established within the sensor 4 will be measured as a means for determining analyte concentration. A semi-permeable membrane 8 forms at least a portion of the wall of a sensor 4 which has an internal processing chamber 10. The semi-permeable membrane 8 is permeable to analyte 12 thereby permitting the same to pass through the membrane 8 and enter the chamber 10. Diffusion of the analog-analyte molecules 14 out of the chamber 10 through the semi-permeable membrane 12 is resisted. The analog-analyte molecules 14 are covalently bonded to dye molecules 16. In the form illustrated the receptor molecules 20 are also covalently bonded to dye molecules 22. The receptor molecules 20 may be free floating or immobilized to a gel (not shown) within chamber 10 or may be immobilized on an interior surface of the sensor 4. They may be bonded to the interior surface of the semi-permeable membrane 8, if desired. While for clarity of illustration only a single analog-analyte molecule 14 and a single receptor molecule 20 have been shown it will be appreciated that a large number of each will preferably provided within processing chamber 10.

Referring still to FIG. 1, in operation a suitable light source 30 which may be a light emitting diode causes a light beam 32 to pass through skin 6 and through transparent or translucent upper wall 34 of sensor 4 to thereby illuminate a portion of the interior of the chamber 10 and contact at least one dyes 16, 22 to establish responsive fluorescent light which emerges through the skin 6 in beam 42 and is received by detector means 44 for processing to determine analyte concentration. The light source means 30 as shown in FIG. 1 is remote in that it is not in physical contact with the sensor 4. It will be appreciated that in this embodiment neither a reflector nor fiber optic means have been employed.

It should be understood that although FIG. 1 relates to measurement of free analog-analyte, the present invention also embraces use of the sensor 4 to measure the bound analog-analyte. In that case, the dye-labeled 16 analog-analyte 14 would bind with receptors 20 coated onto the wall of the sensor 4 within the illuminated region. It may be desirable in certain instances to provide a signal of such bound analog-analyte. Such an approach is contemplated by the present invention.

Figure 2:
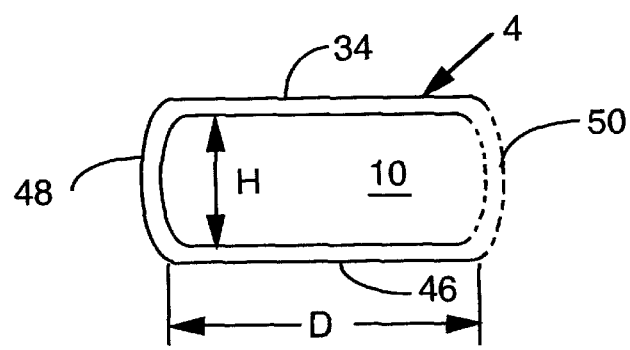
FIG. 2 is a cross-sectional illustration of the sensor of FIG. 1.
Figure 3:
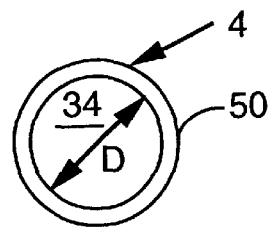
FIG. 3 is a plan view of the sensor of FIG. 1.

Referring to FIGS. 2 and 3, further details of the preferred embodiment of the capsule 4 will be considered. The capsule 4 has a upper wall 34, a lower wall 46 and a circumferential wall 48 at least a portion of which is the semi-permeable membrane 50. The chamber 10 may have an internal diameter D of about 1 to 2 millimeters and a height H of about 1 to 10 millimeters. It will be appreciated that if desired the entire sensor or capsule 4 may be made from the semi-permeable membrane material or in the alternative portions thereof adequate to permit free entry of the analyte may be composed of the semi-permeable membrane. The top wall 34, is at least partially transparent or translucent so as to permit entry of the imposed light and exit of the responsively created fluorescent light.

It will be appreciated that in the present invention a single chamber 10 may be employed without the need to provide dividers which separate a light zone from a dark zone.

Figure 4:
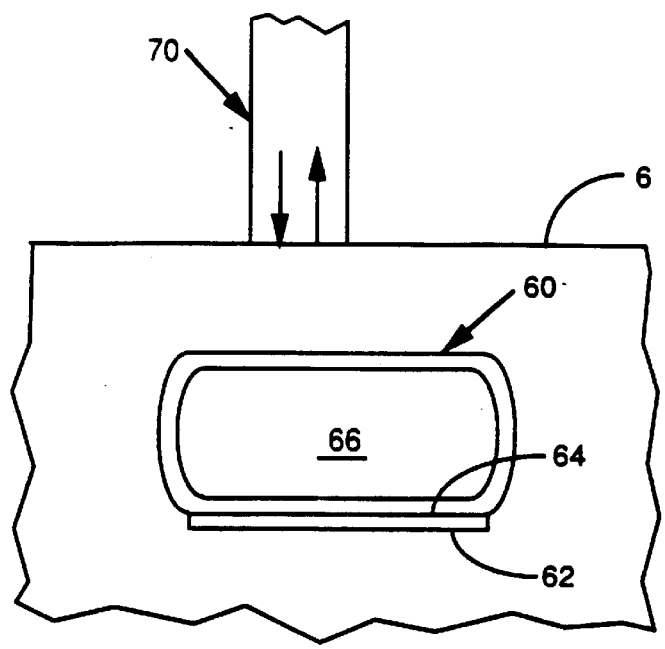
FIG. 4 is a schematic view of a modified embodiment of the sensor of the present invention.

Referring to FIG. 4, two additional refinements of the invention will be considered. In this embodiment, a capsule 60 is positioned under the skin to a depth of about 1 to 2 millimeters and has a reflective member 62 secured to the exterior undersurface of wall 64 of the capsule 60. In this manner, light entering chamber 66 and responsive fluorescent light generated will be caused by reflector 62 to be directed in an upward direction. If desired, reflective member 62 may be positioned on the inside of chamber 66 overlying wall 64 in which case wall 64 would not have to be translucent or transparent. The reflector 62 may be made of any suitably reflective material. If the reflective material is to be positioned within the capsule, it should be inert to body fluids. The material may be metallic or ceramic particles immobilized on the surface of an ultrafiltration membrane.

Also shown in FIG. 4 is the use of optical fiber means 70 for both delivering impinging light through the skin 6 to the sensor 60 and returning responsively created fluorescent light therefrom. While the returning light passing through optical fiber means 70 can be distinguished from the delivered light due to shift in spectra, if desired, the impinging light may be pulsed. Such pulsing will also resist decomposition of reagents disposed within sensor 4. A further option, if desired, would be to employ known time-resolved fluorimetry means.

EXAMPLE 1

The particular receptor material/dye-labeled analog-analyte system of this example has been previously known in other sensors. See D. Meadows, et al., Talenta, 35:145 (1988). In this example, the fluorescence of the system is measured. The analyte being measured is glucose. The analog-analyte used is dextran. The dextran molecules are covalently attached to fluorescein dye molecules. The receptor material used is Concanavalin A (Con A). The Con A molecules are covalently attached to Rhodamine dye molecules. The capsule is transparent, has a semi-permeable membrane, and contains the materials disclosed. The capsule is then placed about 1 mm under the skin of a patient. The interstitial fluid is allowed to come to equilibrium. A light source connected to an optic fiber is used to illuminate the sensor unit through the skin. A fluorimeter connected to an optic fiber as previously disclosed herein is used as the detection means.

Figure 5:
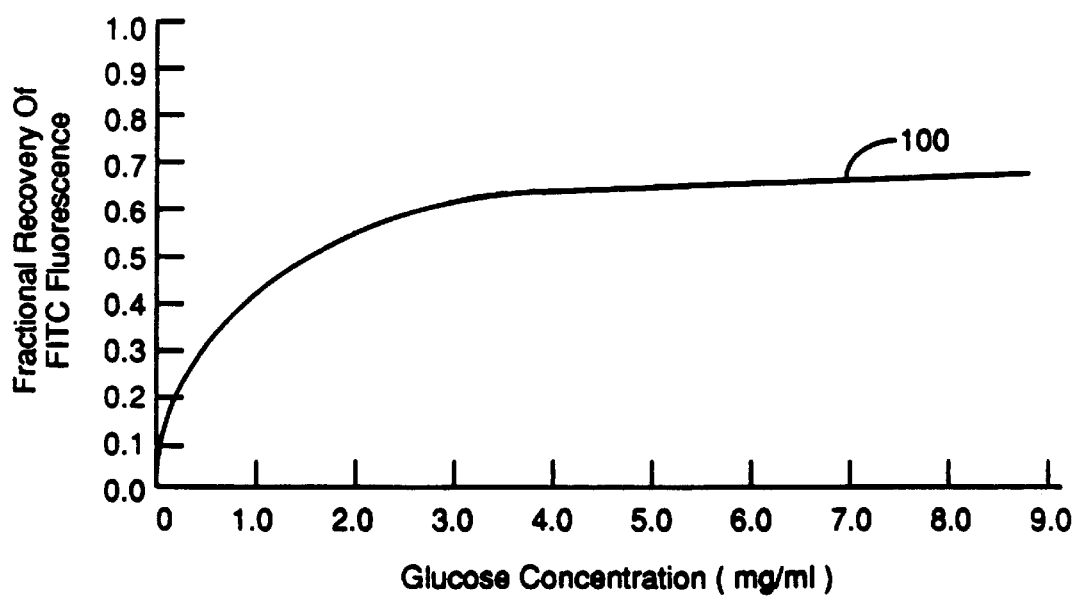
FIG. 5 is a plot of recovered light as related to glucose concentration in the specimen.

When the concentration of glucose in blood is low, most of the dextran will be bound to the Con A. On illumination of the sensor unit by external light source, the emission fluorescence from the fluorescein will be quenched through energy transfer to Rhodamine, and very little emitted light (at a higher wavelength) will be detected outside the skin by the fluorimeter. When the concentration of glucose in blood is high, the dextran is released from the Con A and upon excitation by the external light source, some of the emitted fluorescence from the fluorescein will be detected by the fluorimeter. This general relationship between fluorescence and glucose concentration is illustrated in FIG. 5 wherein curve 100 represents a plot of glucose concentration versus fractional recovery FITC fluorescence. It will be noted that once the glucose level had reached at least about 2.0 mg/ml, the fluorescence reached the level of about 0.5.

If electrical properties of the system are being measured, the capsule need not be transparent or translucent. The capsule, however, must not be an electrical insulator. The electrical properties of the system can be measured by electrical sensors placed on the skin above the sensor unit. At a depth of about 1 mm small changes in conductivity, capacity, frequency or other electrical properties can be measured through the tissue.

The production of detectable compounds by enzymes can take a wide variety of forms depending on the analyte. Using enzymes has the advantage that reversible reactions need not be employed. The body can provide an endless stream of substrate for the enzyme reaction and the receptor (enzyme) is not consumed in the reaction.

EXAMPLE 2

The analyte to be measured is glucose. The capsule is about 1–2 mm in diameter and contains glucose oxidase immobilized to a polyacrylate gel. The capsule also contains a pH indicator in solution. The semi-permeable membrane prevents the pH indicator from diffusing out of the capsule. The capsule is inserted about 1 mm under the skin of a patient with a needle device. Once inserted under the skin, glucose and oxygen diffuse into the capsule through the semi-permeable membrane. Gluconic acid and hydrogen peroxide are formed by the reaction $$2O_2 + \frac{glucose}{oxidase} gluconic\ acid + H_2O_2$$

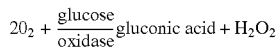

The gluconic acid formed will change the pH in the capsule and the pH indicator will change color. This color change will be measured by a remote light source and detection means above the skin. The gluconic acid and hydrogen peroxide can freely diffuse out of the capsule.

EXAMPLE 3

The analyte to be measured is urea. The capsule is about 1–2 mm in diameter and contains urease and a pH indicator in solution. The semi-permeable membrane prevents the pH indicator and urease from diffusing out of the capsule. The capsule is inserted about 1 mm under the skin of a patient with a needle device. Once inserted under the skin, urea diffuses into the capsule through the semi-permeable membrane. Carbon dioxide and ammonia are formed via the reaction $$urea \xrightarrow{urease} CO_2 + NH_3$$

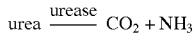

The ammonia formed will change the pH within the capsule and the pH indicator will change color accordingly. This color change will be measured by a remote light source and detection means above the skin. The carbon dioxide and ammonia can freely diffuse out of the capsule.

EXAMPLE 4

Antibodies may be used as receptors to allow for a monitoring of wide variety of molecules, including drugs.

The analyte to be measured is the drug dinitrophenol (DNP). The capsule is about 1–2 mm in diameter and has a height of about 1 to 10 mm and contains DNP-antibody in solution. The semi-permeable membrane prevents the DNP-antibody from diffusing out of the capsule. The capsule is inserted about 1 mm under the skin of a patient with a needle device. Once inserted under the skin, DNP may diffuse into the capsule through the semi-permeable membrane and bind to the DNP-antibodies. Unbound DNP-antibody is naturally fluorescent and this fluorescence is measured by a remote light source and fluorimeter. The fluorescence of DNP is quenched when it binds to an antibody. The antibody will fluoresce at a first level when not bound to said drug and a second level lower than said first when the antibody is bound to the drug. A calibration is made for the quenching of this fluorescence by DNP and the concentration of DNP is calculated.

This example, therefore, shows analyte concentration measurement directly in interaction with an antibody (receptor) without the need for an analog-analyte.

An immunoassay approach may also be employed in the sensor units of the present invention.

EXAMPLE 5

The analyte to be measured is glucose. The capsule is about 1–2 mm in diameter and contains a glucose oxidase/ DNP complex, DNP-antibody, and a pH indicator in solution. The semi-permeable membrane prevents these materials from diffusing out of the capsule. The capsule is inserted about 1 mm under the skin of a patient with a needle device. Once the capsule is inserted under the skin, glucose and oxygen can diffuse freely into the capsule through the semi-permeable membrane. When the blood glucose level is low, most of the DNP-antibody is bound to DNP/glucose oxidase complex blocking the active site of the glucose oxidase. When the blood glucose level is high, glucose competes with the glucose oxidase/DNP complex and frees much of the glucose oxidase/DNP complex. With their active sites unblocked, the glucose oxidase can convert glucose and oxygen into gluconic acid and hydrogen peroxide. The gluconic acid formed will change the pH in the capsule and the pH indicator will change color. This color change will be measured by a remote light source and detection means above the skin. The gluconic acid and hydrogen peroxide can freely diffuse out of the capsule.

Referring now more specifically to the method of the present invention. A sensor 4 (FIG. 1) is introduced under the skin 6. Readings may be taken periodically as the device is primarily to be used for continuous monitoring of the concentration of the analyte 12 in the sample. The analyte 12 is permitted to diffuse across membrane 8 and into chamber 10. A competitive reaction is allowed to proceed. During this reaction, the analog-analyte 14 which contains a fluorescent dye 16 competes with analyte 12 to bind with a receptor 20 which is bonded to dye 22. As the reaction occurs, molecules of analog-analyte 14 which remain unbound fluorescence. This fluorescence is monitored by the external detector means to provide a quantitation measure of glucose concentration. In general, the response time of the sensor 4 is preferably at least less than about five minutes.

A fluorescent signal is emitted in all directions from the fluorescent molecule. In the form shown in FIG. 4, some fluorescent light would be transmitted directly into optical fiber 70, but some of the signal is also emitted in the opposite direction. This signal emitted in the opposite direction is bent 180° by reflective member 62 so that it, too, will travel in the direction of optical fiber 70 and be received by optical fiber 70. The signal sensed by optical fiber 70 is preferably filtered to remove excitation light and is then converted to a voltage signal by the detector means with which it is operatively associated in a manner known to those skilled in the art. Thereafter, the voltage signal is processed and the information is used as appropriate in the particular application.

In another embodiment of the invention, the sensor unit does not have to have a semi-permeable membrane as a portion thereof. The sensor could be composed of a polymer-gel structure which has a reporter molecule covalently bound to the exterior of the structure. Among the suitable gel forming polymers are polyacrylamide, cellulose, polyethylene glycol and gelatin. A receptor which has a reporter molecule on or in close proximity to it is covalently bound to the sensor unit. When the analyte is bound to the receptor, the optical property would change. As this embodiment does not require passage of the analyte into an interior chamber, it may be employed with analytes that are macromolecules.

An example of this embodiment would be suture fibers disposed under the skin having receptors and reporter reagent covalently bound to the exterior of the suture which is made from a stable polymer gel fiber. Alteration of the optical properties when an analyte bound to the receptors could be measured by detector means with subsequent processing in accordance with other embodiments of the invention. This embodiment may be employed, for example, in measuring DNP as in EXAMPLE 4, with the receptor being a DNP antibody.

While for simplicity of disclosure, reference has been made specifically herein to the use of a single receptor with an associated dye, the invention is not so limited. If desired, more than one receptor, each with an associated dye, could be employed. For example, within a single sensor capsule, two or more receptor means, each having an associated different dye, may be provided. If two different receptors are employed, a first receptor material could have an associated dye of a first wavelength and a second receptor material could have an associated second dye of a second wavelength different from the first wavelength. In this manner, the properties of two analytes could be measured simultaneously. More than two receptor materials and associated dyes could be employed to detect more than two analytes, if desired.

It will be appreciated from the foregoing that the device and method of the present invention provide a sensor system which can be used effectively for sensing of biochemicals, in vivo. It does not require chronic connections through the Datient's skin.

Although the present invention has been described herein primarily in the context of biomedical applications, it should be understood that the invention may also be used in a variety of other applications such as in environmental testing of, for example, PCB content in oils, and in other industrial applications.

Whereas particular embodiments of the invention have been described hereinabove for purposes of illustration, it will be evident to those skilled in the art that numerous variations of the details may be made without departing from the invention as defined in the appended claims.

What is claimed is:

1. A sensor unit for sensing properties of a sample analyte and to be used with remote detection means, said sensor unit comprising
    a capsule defining a processing chamber, at least a portion of said capsule being a semi-permeable membrane, which is permeable to said analyte,
    receptor material disposed within said chamber and capable of chemically interacting with said analyte,
    said sensor unit further comprises a pH indicator within said sensor unit, and
    said pH indicator being of such size that diffusion of said pH indicator out of said chamber is resisted by said semi-permeable membrane.

2. The sensor unit of claim 1 wherein said analyte is glucose and said receptor material is glucose oxidase.

3. A system for sensing properties of an analyte comprising
    a sensor capsule having a processing chamber defined by a wall which has a semi-permeable membrane permeable to said analyte as at least a portion thereof,
    receptor material disposed within said chamber and being capable of chemically interacting with said analyte,
    at least a portion of said sensor wall being translucent, and
    electric sensor means for positioning on the skin in relatively close proximity to said sensor capsule for monitoring electrical properties of said analyte.

4. The system of claim 3 including said electrical sensors having means for monitoring at least one electrical property consisting of a property selected from the group consisting of conductivity, frequency, and capacity.

* * * * *

UNITED STATES PATENT AND TRADEMARK OFFICE
CERTIFICATE OF CORRECTION

PATENT NO. : 6,256,522 B1
DATED : July 3, 2001
INVENTOR(S) : Jerome S. Schultz

Page 1 of 1

It is certified that error appears in the above-identified patent and that said Letters Patent is hereby corrected as shown below:

Column 1,
Line 64, "wail" should read -- wall --.

Column 6,
Line 12, "analoganalyte" should read -- analog-analyte --.

Column 7,
Line 41, "Light" should read -- light --.

Column 8,
Line 48, insert -- the -- after "into".

Column 13,
Line 27, "Datient's" should read -- patient's --.

Signed and Sealed this

Twenty-third Day of April, 2002

Attest:

JAMES E. ROGAN
Attesting Officer
Director of the United States Patent and Trademark Office